(12) United States Patent
Obel et al.

(10) Patent No.: US 6,853,861 B1
(45) Date of Patent: Feb. 8, 2005

(54) IMPLANTABLE CARDIAC STIMULATOR WITH SYNCHRONIZATION OF THE VENTRICULAR CONTRACTIONS

(75) Inventors: Martin Obel, Danderyd (SE); Jan Skansén, Ingarö (SE)

(73) Assignee: St. Jude Medical AG, Järfälla (SE)

( * ) Notice: Subject to any disclaimer, the term of this patent is extended or adjusted under 35 U.S.C. 154(b) by 455 days.

(21) Appl. No.: 10/048,780

(22) PCT Filed: Jun. 19, 2000

(86) PCT No.: PCT/SE00/01309

§ 371 (c)(1),
(2), (4) Date: Feb. 1, 2002

(87) PCT Pub. No.: WO01/10499

PCT Pub. Date: Feb. 15, 2001

(30) Foreign Application Priority Data

Aug. 5, 1999 (SE) ............................. 9902848

(51) Int. Cl.[7] .............................................. A61N 1/375
(52) U.S. Cl. ....................................................... 607/27
(58) Field of Search .............................. 607/9, 18, 27, 607/123, 148

(56) References Cited

U.S. PATENT DOCUMENTS

| | | | |
|---|---|---|---|
| 4,928,688 A | 5/1990 | Mower | |
| 5,720,768 A | 2/1998 | Verboven-Nelissen | |
| 5,728,140 A | 3/1998 | Salo et al. | |
| 5,902,324 A | 5/1999 | Thompson | |

OTHER PUBLICATIONS

"A Method For Permanent Transvenous Left Ventricular Pacing," Blane et al, PACE, vol. 21 (1998), pp. 2021–2024.

*Primary Examiner*—Mark Bockelman
(74) *Attorney, Agent, or Firm*—Schiff Hardin LLP

(57) ABSTRACT

An implantable cardiac stimulating device has a control circuit connected to first and second electrodes respectively for stimulating first and second ventricles of a heart. Evoked response sensors respectively sense evoked response parameters to stimulation of the two ventricles. Delivery of stimulating pulses via the respective electrodes to the respective ventricles in the same cycle of the heart is controlled so that there is a time interval between the pulses respectively delivered to the two ventricles. The control circuit controls delivery of the stimulating pulses so that the respective evoked response parameters of the two ventricles occur substantially simultaneously.

20 Claims, 3 Drawing Sheets

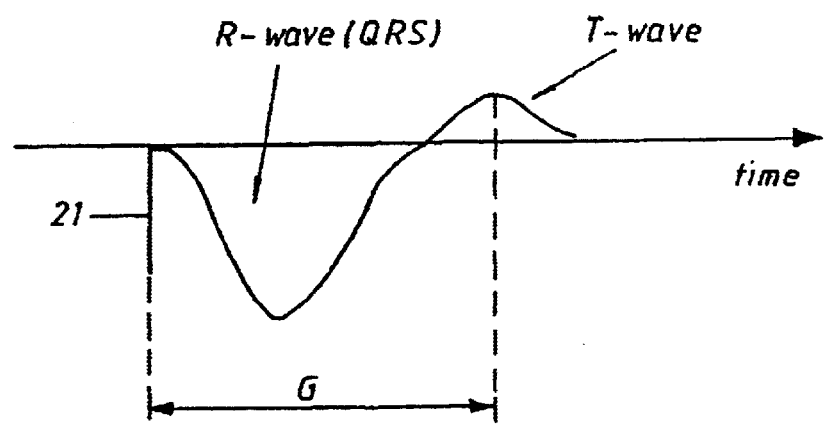
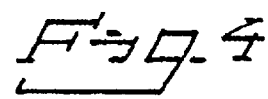
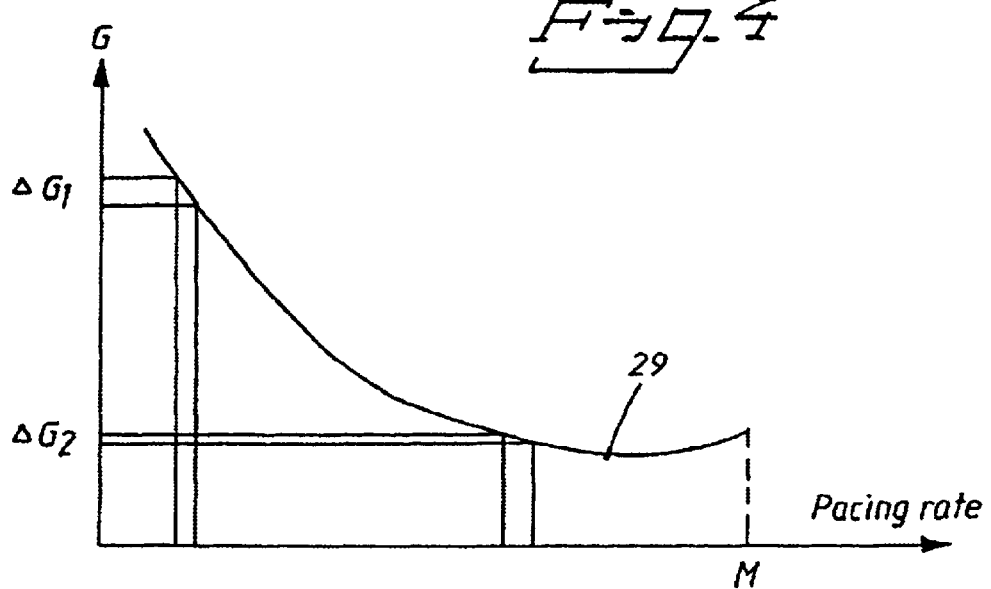

IMPLANTABLE CARDIAC STIMULATOR WITH SYNCHRONIZATION OF THE VENTRICULAR CONTRACTIONS

BACKGROUND OF THE INVENTION

1. Field of the Invention

The present invention relates to an implantable cardiac stimulating device of the type having a housing, a control circuit enclosed in the housing, the control circuit being adapted for connection to a first electrode positioned to stimulate a first ventricle of the heart and to a second electrode positioned to stimulate the second ventricle of the heart, and wherein control circuit controls the delivery of stimulating pulses to the first and second electrodes, and means for sensing at least one evoked response parameter to the stimulation of the first and second ventricles.

2. Description of the Prior Art

Most pacers are arranged to stimulate the right ventricle of the heart, but it is also known to stimulate the left ventricle. In particular for the treatment of congestive heart failure or other severe cardiac failures it is known to stimulate the left ventricle, or both ventricles, in order to optimize the hemodynamic performance of the heart.

U.S. Pat. No. 5,728,140 describes a method and an apparatus for pacing the left ventricle of the heart. The pacing electrode is positioned within the interventricular septum proximate the left ventricular wall thereof.

United States Patent No. describes different possible electrode positions in order to stimulate or sense the different chambers of the heart.

Also the article "A Method for Permanent Transvenous Left Ventricular Pacing" by Blanc et al, PACE, Vol. 21, 1998, pp. 2021–2024, describes a method for positioning leads for left ventricular pacing.

U.S. Pat. No. 4,928,688 describes a method and an apparatus for treating patients suffering from congestive heart failure by stimulating both the ventricles. The document discusses the problem involved when the left and right ventricles contract asynchronously. In order to effect substantially simultaneous contraction of both ventricles, the document suggests means for separately processing sensed cardiac signals from each of the right and left ventricles. If ventricular contractions are not sensed in both ventricles within a period of coincidence defined by a time delay, the pacing pulse will be emitted at the end of this time delay, but only to the ventricle for which a QRS-complex has not been sensed. The time delay is suggested to be in the order of 5–10 ms.

SUMMARY OF THE INVENTION

The purpose of pacing the left and right ventricles with separate leads is to improve the synchronization of the mechanical contraction of the two ventricles. The synchronization of the ventricles is very important for patients with severe congestive heart failure. These patients are often waiting for a heart transplant and optimal hemodynamic conditions during the time before the transplant is important for the outcome. A problem in this context is that synchronous pacing will not necessarily provide the best possible synchronization of the actual contraction of the ventricles. The present invention is based on the recognition that the synchronization of the ventricles may be improved compared to known devices if the cardiac stimulating device adjusts the timing of the stimulating pulses in order to optimize the synchronization in the contraction of the ventricles it is thus an object of the present invention to provide an implantable cardiac stimulating device by wherein the synchronization of the ventricles is improved.

The above object is achieved in accordance with the invention in an implantable cardiac stimulating device having a housing containing a control circuit which is connectible to first and second electrodes, which are respectively positionable to stimulate first and second ventricles of the heart, the control circuit including first and second pulse generators for respectively supplying stimulating pulses to the first and second ventricles via the first and second electrodes, the control circuit including a pulse delivery controller which controls delivery of the stimulating pulses via the first and second electrodes within the same heart cycle with a time interval between the pulses respectively supplied to the first and second ventricles, the control circuit varying this time interval, a first evoked response sensor for sensing at least one evoked response parameter to stimulation of the first ventricle, a second evoked response sensor for sensing at least one evoked response parameter to stimulation of the second ventricle, a comparator for comparing respective times of occurrence of the evoked response parameters respectively sensed by the first and second evoked response sensors and identifies a difference between the times of occurrence, and wherein the control circuit controls delivery of the stimulating pulses by the first and second electrodes, respectively, so that the aforementioned difference is minimized.

According to the invention, the stimulating pulses to the ventricles are delivered at such times that the respectively sensed evoked response parameters to the left and right ventricles occur substantially simultaneously. Since the evoked responses are better related to the actual contraction of the ventricles then the delivery of the pacing pulses, an improved synchronization may be obtained by the present invention.

According to a further embodiment of the invention, the evoked response sensors for respectively sensing at least one evoked response parameter to stimulation for the first and second ventricles sense an electrical evoked response parameter. Such an electrical evoked response parameter may be sensed by, for example, the electrodes used for stimulating the ventricles.

According to a further embodiment of the invention, the control circuit compares the R-wave in the evoked response to the stimulation of the first ventricle with the R-wave in the evoked response to stimulation of the second ventricle. The R-wave is also called the QRS-complex. The R-wave is more closely related to the ventricular contraction than the delivered stimulating pulse. By making the R-waves in the left and right ventricles occur substantially simultaneously, a good synchronization of the ventricles is obtained.

In another embodiment of the invention, the 5 control circuit makes the comparison by measuring an integral of the difference between the R-wave in the evoked response to the stimulation of the first ventricle and the R-wave in the evoked response to stimulation of the second ventricle, and the time interval is set such that this integral is minimized. Since the R-wave in the evoked response to stimulation of the left ventricle may have a slightly different shape than the R-wave in the evoked response to stimulation of the right ventricle, by minimizing the aforementioned integral a substantially simultaneous contraction of the left and right ventricles is obtained.

According to a further embodiment of the invention, this integral is measured over a predetermined time period after stimulation. This predetermined time period can be related either to the stimulation of the left ventricle or of the right ventricle. Thus it is not necessary to exactly detect the beginning and the end of the R-waves. However, the predetermined time period is selected to essentially correspond to the extension in time of the R-waves.

According to a further embodiment of the invention, the control circuit makes the comparison by comparing the occurrence in time of a slope or peak of the R-wave in the evoked response to the stimulation of the first ventricle with the occurrence in time of the corresponding slope or peak of the R-wave in the evoked response to stimulation of the second ventricle, and the time interval is set such that the difference in the respective times of occurrence between these slopes or peaks is minimized. Instead of using the above-mentioned integral, it is possible to detect another point on the R-wave curve. For such a point it is suitable to use either a slope or a peak. The slope may be either negative or positive. For example, the maximum negative or positive slope may be used.

According to another embodiment of the invention, the control circuit sets the time interval by first varying the time interval and comparing the corresponding evoked response parameters for the different time intervals, and then sets the time interval such that the aforementioned integral is minimized or the aforementioned difference in the times of occurrence between the slopes or peaks is as small as possible. In this way an optimal time interval can be found by an iterative process. The difference in the times of occurrence between the slopes or peaks may be continuously monitored, with the time interval being adjusted such that the contractions of the left and right ventricles occur substantially simultaneously.

According to a further embodiment of the invention, the evoked response sensors each sense an evoked response parameter that is a unipolar sensed evoked response parameter. It has been found that a unipolar sensed evoked response parameter is suitable for detecting the R-wave. However, it is also possible to use bipolar sensing.

According to a further embodiment of the invention, the control circuit compares the T-wave in the sensed evoked response to the stimulation of the first ventricle with the T-wave in the sensed evoked response to stimulation of the second ventricle. The T-wave represents ventricular repolarization. This wave is a good indication of the ventricular contraction.

According to another embodiment of the invention, the control circuit makes the comparison by measuring an integral of the difference between the T-wave in the evoked response to the stimulation of the first ventricle and the T-wave in the evoked response to stimulation of the second ventricle, and the time interval is set such that this integral is minimized. In the same manner as described above in connection with the R-wave, it is possible to make the contraction of the ventricles occur substantially simultaneously by minimizing the corresponding integral for the T-waves.

According to a further embodiment of the invention, this integral is measured over a predetermined time period after stimulation.

Furthermore, in a similar manner as to that described above in connection with the R-wave, it is possible to detect a slope or peak of the T-wave in the evoked response to stimulation of the ventricles. Also, in a manner similar to that described above it is advantageous to set the time interval by varying the time interval and by comparing the corresponding evoked response parameters.

According to a further embodiment of the invention, the each of the evoked response sensors senses an evoked response parameter that is a bipolar sensed evoked response parameter. Such bipolar sensing has been shown to be advantageous for detecting the T-wave. However, it is also possible to use unipolar sensing.

According to another embodiment of the invention, the respective evoked response sensors for sensing at least one evoked response parameter to stimulation for the first and second ventricles sense a mechanical evoked response parameter. The mechanical evoked response parameter may constitute the actual contraction of the respective ventricle. Such a mechanical response parameter may be sensed by, for example, an accelerometer, a pressure sensor or an impedance sensor. An advantage to sensing a mechanical evoked response parameter is that this parameter is directly indicative of the contraction of the ventricles.

In a further embodiment of the invention, the control circuit includes a unit for varying the rate of the stimulation pulses up to a maximum pacing rate, a timer which measures a time gap between a stimulating pulse and the associated evoked response parameter sensed by at least one of the first or second evoked response sensors, a monitor which monitors the time gap at varying pacing rates with which the stimulating pulses are delivered, and wherein the control circuit lowers the maximum pacing rate if the time gap does not decrease with increasing pacing rate.

The present invention is based on the recognition that the time gap between a stimulating pulse and the associated evoked response parameter can be monitored in order to detect heart problems, such as dissynchronization. Normally, when the pacing rate increases, the time gap between a stimulating pulse and the associated evoked response parameter becomes shorter. However, at a certain pacing rate, this time gap may stop decreasing although the pacing rate increases. The present invention is based on a recognition that such a situation is an indication of heart problems, such as a dissynchronization between the ventricles. According to this embodiment of the invention, an implantable cardiac stimulating device is provided which exposes the patient wearing the device to less risk, since the maximum pacing rate is lowered if the time gap does not decrease with increasing pacing rate.

DESCRIPTION OF THE DRAWINGS

FIG. 3 schematically illustrates an electrocardiographic response signal to a stimulating pulse.

FIG. 4 schematically illustrates the relationship between the time gap and the pacing rate.

DESCRIPTION OF THE PREFERRED EMBODIMENTS

Figure 1:
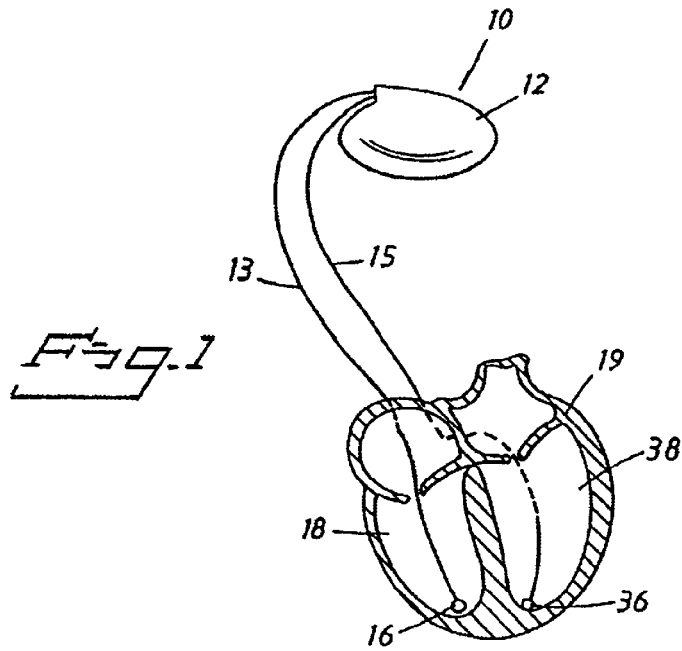
FIG. 1 is a schematic representation of a device according to the invention connected to a heart.

FIG. 1 shows an implantable cardiac stimulating device 10, here in after also called a pacemaker, according to the invention. The pacemaker 10 has a housing 12. A control circuit 14 (see FIG. 2) is enclosed in the housing 12. The control circuit 14, and thereby the pacemaker 10, is adapted to be connected to a first electrode 16. FIG. 1 shows such an electrode 16 which is connected to the pacemaker 10 via a lead 13. The first electrode 16 is adapted to be positioned to stimulate a first ventricle 18 of the heart 19. The first ventricle 18 is in this case the right ventricle. According to the invention, the pacemaker 10 is also adapted to be connected to a second electrode 36. FIG. 1 shows such a second electrode 36 connected to the housing 12 via a lead 15. The second electrode 36 is positioned to stimulate a second ventricle 38 of the heart 19. The second ventricle 38 is in this case the left ventricle. The electrodes 16, 36 may include more than one electrical conductor in order to allow for bipolar pacing and sensing.

Figure 2:
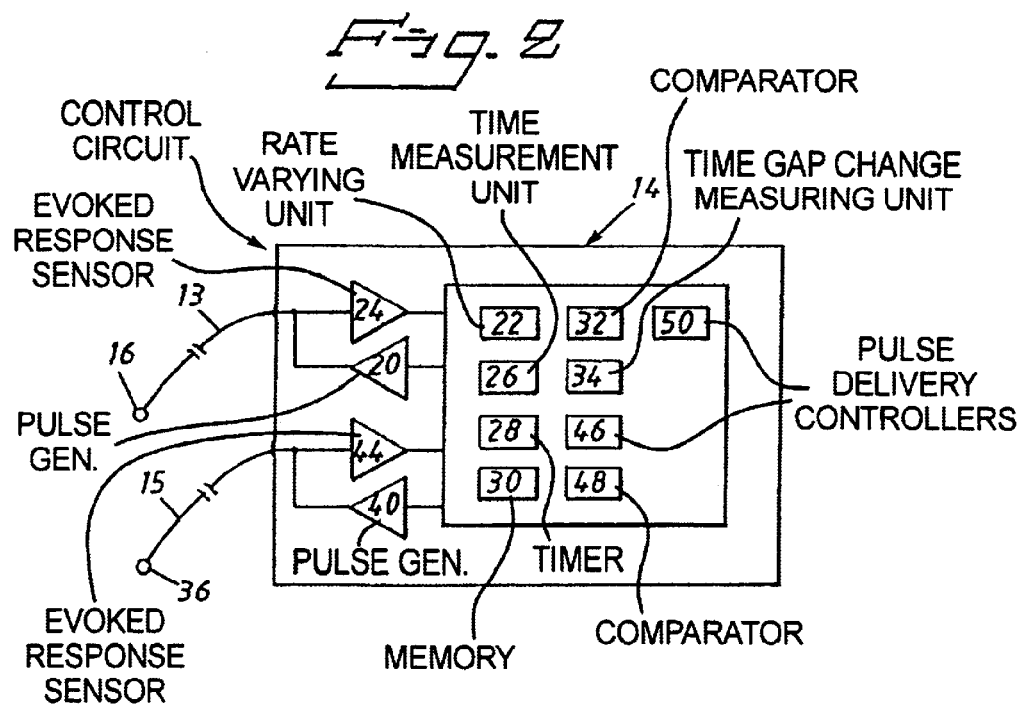
FIG. 2 is a block diagram of a device according to the invention.

FIG. 2 shows a schematic representation of a block diagram of a control circuit 14 which is enclosed in the housing 12 of the pacemaker 10. The control circuit 14 includes pulse generators 20, 40 for delivering stimulating pulses 21 to the first 16 and second 36 electrodes. The control circuit 14 has an evoked response sensor 24 arranged for sensing at least one evoked response parameter of said first ventricle 18 to the stimulating pulses delivered via said first electrode 16. The pacemaker 10 also has an evoked response sensor 44 arranged for sensing at least one evoked response parameter to the stimulation of the second ventricle 38. The evoked response parameter may either be a parameter which indicates a mechanical contraction of the ventricle 18 or a parameter indicating an electrical response. The mechanical contraction may, for example, be sensed by an accelerometer, a pressure sensor or an impedance sensor. The impedance may, for example be respectively sensed by the electrodes 16, 36 connected to the pacemaker 10. The evoked response parameter may also be an electrical evoked response parameter which is sensed, for example, by the respective electrodes 16, 36 positioned in the ventricles. Such an electrical evoked response parameter may be, for example, the T-wave or the R-wave in the electrical evoked response signal.

Figure 5A:
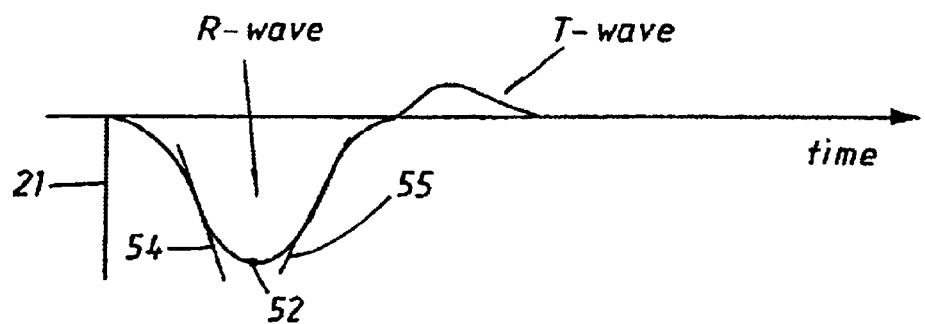
FIGS. 5a, 5b and 5c respectively schematically illustrate typical electrocardiographic response signals to stimulation of the left and right ventricles.
Figure 5B:
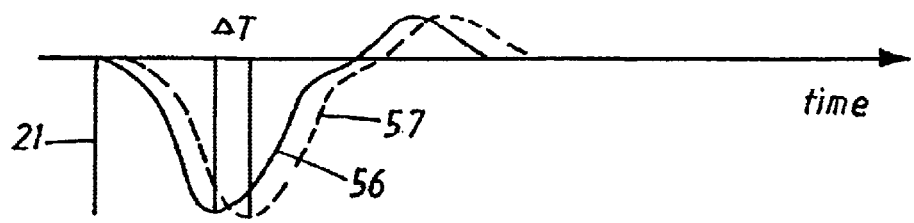
Figure 5C:
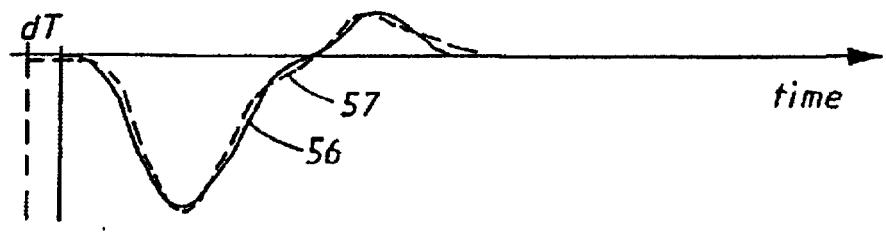

The control circuit 14 also has a pulse delivery controller 46 arranged to enable the delivery of the stimulating pulses to the first electrode 16 and the second electrode 36 within the same cycle of the heart such that there may be a time interval dT between the pulses respectively delivered by the electrodes 16 and 36 (see FIG. 5c). Furthermore, the control circuit 14 varies the time interval dT is variable. The control circuit 14 has a comparator 48 arranged to compare the occurrence in time of the sensed evoked response parameter to the stimulation of the first ventricle 18 with the sensed evoked response parameter to the stimulation of the second ventricle 38. The control circuit 14 also has a pulse delivery controller 50 arranged to control the delivery of the stimulating pulses to the first electrode 16 and second electrode 36 such that the difference in occurrence in time ΔT between the sensed evoked response parameter to the stimulation of the first ventricle 18 and said sensed evoked response parameter to the stimulation of the second ventricle 38 is minimized.

The invention is further illustrated in FIGS. 5a, 5b, 5c. The evoked response parameter may be a mechanical or an electrical sensed evoked response parameter as explained above. FIGS. 5a, 5b, 5c show typical electrical evoked responses. The electrical evoked response parameter may be related to either the R-wave CQRS-complex) or the T-wave. Moreover, different alternatives exist for detecting the evoked response. The evoked response parameter may for example be a peak or a maximum 52 or a certain predetermined slope 54, 55 of the wave which is detected. Also other possible points on the curve in the electrical evoked response may be detected, e.g. a zero-crossing. Instead of directly comparing the occurrence in time of a slope or peak or other point on the respective wave, it is possible to measure an integral of the difference between the wave in question in the evoked response to the stimulation of the first ventricle 18 and the wave in the evoked response to the stimulation of the second ventricle 38. The time interval dT is thereby set such that said integral is minimized. The integral is preferably measured over a predetermined time period after a stimulating pulse. For example, for detecting the R-wave the time period may start 10 ms after the delivery of the last stimulating pulse and end 40 ms later. The sensing of the evoked response may be done either with a unipolar or with a bipolar arrangement. When the R-wave is sensed it may be advantageous to use unipolar sensing. When the T-wave is sensed it may be advantageous to use bipolar sensing.

In FIG. 5b an example is shown where the peak of the R-wave 5 is detected. The curve 56 represents the electrical evoked response to a stimulation pulse 21 for the first ventricle 18. The curve 57 represents the corresponding evoked response for the second ventricle 38. According to this example, the stimulating pulses 21 to the first 16 and the second 36 electrodes are delivered simultaneously. In the example shown, the peak of the curve 56 occurs before the peak of the curve 57. The difference in occurrence in time between the peaks of the curves 56 and 57 is represented by ΔT. According to this embodiment of the invention, the pulse delivery controller 50 in control circuit 14 delivers the stimulating pulses to the first electrode 16 and the second electrode 36 at different times such that the difference in occurrence in time of the peaks of the curves 56 and 57 is minimized.

FIG. 5c illustrates that the stimulating pulse to the second ventricle 58 is delivered before the stimulating pulse to the first ventricle 18. The two peaks of the curves 56 and 57 occur substantially simultaneously (ΔT is equal to 0). In order to make the peaks occur simultaneously it is possible to either deliver the stimulating pulse to the electrode 36 (corresponding to the curve 57) earlier in time or to deliver the pulse to the electrode 16 (corresponding to the curve 56) later in time. A physician may determine which of the two possibilities is most suitable for a particular patient.

The control circuit 14 can include a rate varying unit 22 for varying the pacing rate. The time interval dT may vary in dependence of the pacing rate. The control circuit 14 can take the pacing rate into account when determining a suitable time interval dT. In other words, if the pacing rate increases, the control circuit 14 may be set to change the time interval dT such that the sensed evoked response parameters are likely to occur simultaneously. The evoked responses may then be continuously monitored such that the time interval dT is modified such that the evoked response parameters continuously occur simultaneously.

According to a further embodiment of the invention, the rate varying unit 22 varies the rate of stimulating pulses up to a maximum pacing rate M. The maximum pacing rate M may be the maximum sensor rate and/or the maximum track rate. The control circuit 14 also has a time measurement unit 26 arranged to measure a first time gap G between a stimulating pulse and the associated evoked response parameter sensed by evoked response sensor 24.

FIG. 3 shows a schematic representation of a typical electrical sensed response signal. A stimulating pulse is represented by the reference number 21. In the electrical response to such a stimulating pulse 21 an R-wave (also called QRS-complex) and a T-wave may be detected. In the example according to FIG. 3 the sensed evoked response parameter is the T-wave. G represents the time gap between the stimulating pulse 21 and the associated evoked response parameter sensed by the evoked response sensor 24.

The control circuit 14 has a timer 28 for monitoring the first time gap G at the varying pacing rates with which the stimulating pulses 21 are delivered. The control circuit 14 lowers maximum pacing rate M if said first time gap G does not decrease with increasing pacing rate.

FIG. 4 shows a schematic representation of the relationship between the time gap G and the pacing rate. The pacemaker 10 normally has a preset, programmable maximum pacing rate M. The maximum pacing rate is represented with M in FIG. 4. The time gap between a stimulating pulse 21 and the associated evoked response parameter normally decreases when the pacing rate increases. However, for some patients, for example those with a progressive heart disease which may alter the compliance patterns due to geometric remodeling of the myocardium, the heart disease may be such that the previously set maximum pacing rate M is in fact too high for the patient. According to this embodiment of the invention, the maximum pacing rate M is lowered if the time gap G does not decrease with increasing pacing rate. In FIG. 4 the point 29 on the curve is a point where the time gap G does not decrease with increasing pacing rate. When this point 29 is reached, the maximum pacing rate M is thus lowered according to the present invention.

The control circuit 14 may also have a time gap change measuring unit 34 for 20 monitoring the change in time gap AG when the pacing rate increases. The control circuit 14 lowers the maximum pacing rate M is lowered if the change in time gap AG is below a predetermined value. In FIG. 4 two examples of AG are indicated. $AG_1$ is relatively large and $AG_2$ is smaller. When AG is below a predetermined value the maximum pacing rate M is thus lowered. The maximum pacing rate M may be lowered before the point 29 is reached. The risks to which the heart is exposed thus are reduced even further.

Returning to FIG. 2, the control circuit 14 may also has a memory 30 for storing the measured first time gap G for one or more pacing rates. The control circuit 14 further has a comparator 32 arranged for comparing the currently measured first time gap with a previously stored first time gap for the corresponding pacing rate. The control circuit 14 lowers the maximum pacing rate M if the difference between the currently measured first time gap and the corresponding stored first time gap exceeds a predetermined value. A further measure thus is taken in order to reduce the risk for the patient.

As explained above in connection with FIG. 1, the pacemaker 10 is adapted to be connected to a second electrode 36. The timer 26 arranged to measure the first time gap G may also measure a corresponding second time gap between a stimulating pulse and the associated evoked response parameter of the second ventricle 38. The control circuit 14 lowers the maximum pacing rate M if at least one of the first and second time gaps does not decrease with increasing pacing rate.

The control circuit 14 may also lower the maximum pacing rate M if the difference between the first and second time gaps exceeds a predetermined value to further reduce the risks to which the patient is exposed. Although modifications and changes may be suggested by those skilled in the art, it is the intention of the inventors to embody within the patent warranted hereon all changes and modifications as reasonably and properly come within the scope of their contribution to the art.

What is claimed is:

1. An implantable cardiac stimulating device comprising:
   a housing;
   a first electrode adapted to be positioned in a first ventricle of a heart;
   a second electrode adapted to be positioned in a second ventricle of a heart;
   a first pulse generator connected to said first electrode for delivering stimulation pulses via said first electrode to stimulate said first ventricle;
   a second pulse generator connected to said second electrode for delivering stimulation pulses via said second electrode to stimulate said second ventricle;
   a control circuit in said housing including a pulse delivery controller connected to said first and second pulse generators which controls delivery of stimulating pulses via said first and second electrodes within the same cardiac cycle with a time interval between the stimulation pulses respectively delivered via said first and second electrodes, and for varying said time interval;
   a first evoked response sensor for sensing at least one evoked response parameter to stimulation of said first ventricle;
   a second evoked response sensor for sensing at least one evoked response parameter to stimulation of the second ventricle;
   said control circuit including a comparator connected to said first and second evoked response sensors for comparing respective times of occurrence of the evoked response parameters respectively sensed by said first and second evoked response sensors and for identifying a time difference between said times of occurrence; and
   said control circuit controlling said pulse delivery controller to minimize said time difference.

2. An implantable cardiac stimulating device as claimed in claim 1 wherein said first evoked response sensor is connected to said first electrode and senses an electrical evoked response parameter to stimulation of said first ventricle, and wherein said second evoked response sensor is connected to said second electrode and senses an electrical evoked response parameter to stimulation of said second ventricle.

3. An implantable cardiac stimulating device as claimed in claim 2 wherein said first evoked response sensor senses a unipolar electrical signal as said electrical evoked response parameter unipolar to stimulation of said first ventricle, and wherein said second evoked response sensor senses a unipolar electrical signal as said electrical evoked response parameter to stimulation of said second ventricle.

4. An implantable cardiac stimulating device as claimed in claim 2 wherein said first evoked response sensor senses a bipolar electrical signal as said electrical evoked response parameter bipolar to stimulation of said first ventricle, and wherein said second evoked response senor senses a bipolar electrical signal as said electrical evoked response parameter to stimulation of said second ventricle.

5. An implantable cardiac stimulating device as claimed in claim 1 wherein said first evoked response sensor senses an electrical signal containing a first R-wave as said electrical evoked response parameter to stimulation of said first ventricle, and wherein said second evoked response senors senses an electrical signal containing a second R-wave as said electrical evoked response parameter to stimulation of said second ventricle, and wherein said comparator compares said first R-wave and said second R-wave.

6. An implantable cardiac stimulating device as claimed in claim 5 wherein said comparator compares said first R-wave to said second R-wave by measuring an integral of a difference between said first R-wave and said second R-wave, and wherein said pulse delivery controller sets said time interval to minimize said integral.

7. An implantable cardiac stimulating device as claimed in claim 6 wherein said comparator measures said integral over a predetermined time period after a stimulation pulse.

8. An implantable cardiac stimulating device as claimed in claim 6 wherein said comparator identifies a plurality of integrals respectively obtained for different time intervals as said pulse delivery controller varies said time interval, and wherein said pulse delivery controller sets said time interval to a time interval among said different time intervals respectively producing a smallest integral of said plurality of integrals.

9. An implantable cardiac stimulating device as claimed in claim 5 wherein said first R-wave has a first R-wave characteristic selected from the group consisting of a slope of said first R-wave and a peak of said first R-wave, and wherein said second R-wave has a second R-wave characteristic selected from the group consisting of a slope of said second R-wave and a peak of said second R-wave, and wherein said comparator compares respective times of occurrence of said first R-wave characteristic and said second R-wave characteristic to identify a time difference therebetween, and wherein said pulse delivery controller sets said time interval to minimize said time difference.

10. An implantable cardiac stimulating device as claimed in claim 9 wherein said comparator identifies a plurality of time differences respectively obtained for different time intervals as said pulse delivery controller varies said time difference, and wherein said pulse delivery controller sets said time interval to a time difference among said different time differences respectively producing a smallest time difference of said plurality of time differences.

11. An implantable cardiac stimulating device as claimed in claim 5 wherein said first evoked response sensor senses a unipolar electrical signal containing said first R-wave as said electrical evoked response parameter to stimulation of said first ventricle, and wherein said second evoked response senor senses a unipolar electrical signal containing said second R-wave as said electrical evoked response parameter to stimulation of said second ventricle.

12. An implantable cardiac stimulating device as claimed in claim 1 wherein said first evoked response sensor senses an electrical signal containing a first T-wave as said electrical evoked response parameter to stimulation of said first ventricle, and wherein said second evoked response senors senses an electrical signal containing a second T-wave as said electrical evoked response parameter to stimulation of said second ventricle, and wherein said comparator compares said first T-wave and said second R-wave.

13. An implantable cardiac stimulating device as claimed in claim 12 wherein said comparator compares said first T-wave to said second T-wave by measuring an integral of a difference between said first T-wave and said second T-wave, and wherein said pulse delivery controller sets said time interval to minimize said integral.

14. An implantable cardiac stimulating device as claimed in claim 13 wherein said comparator measures said integral over a predetermined time period after a stimulation pulse.

15. An implantable cardiac stimulating device as claimed in claim 13 wherein said comparator identifies a plurality of integrals respectively obtained for different time intervals as said pulse delivery controller varies said time interval, and wherein said pulse delivery controller sets said time interval to a time interval among said different time intervals respectively producing a smallest integral of said plurality of integrals.

16. An implantable cardiac stimulating device as claimed in claim 12 wherein said first T-wave has a first T-wave characteristic selected from the group consisting of a slope of said first T-wave and a peak of said first T-wave, and wherein said second T-wave has a second T-wave characteristic selected from the group consisting of a slope of said second T-wave and a peak of said second T-wave, and wherein said comparator compares respective times of occurrence of said first T-wave characteristic and said second T-wave characteristic to identify a time difference therebetween, and wherein said pulse delivery controller sets said time interval to minimize said time difference.

17. An implantable cardiac stimulating device as claimed in claim 16 wherein said comparator identifies a plurality of time differences respectively obtained for different time intervals as said pulse delivery controller varies said time difference, and wherein said pulse delivery controller sets said time interval to a time difference among said different time differences respectively producing a smallest time difference of said plurality of time differences.

18. An implantable cardiac stimulating device as claimed in claim 12 wherein said first evoked response sensor senses a bipolar electrical signal containing said first T-wave as said electrical evoked response parameter to stimulation of said first ventricle, and wherein said second evoked response senor senses a bipolar electrical signal containing said second T-wave as said electrical evoked response parameter to stimulation of said second ventricle.

19. An implantable cardiac stimulating device as claimed in claim 1 wherein said first evoked response sensor senses a mechanical evoked response parameter to stimulation of said first ventricle, and wherein said second evoked response sensor senses a mechanical evoked response parameter to stimulation of said second ventricle.

20. An implantable cardiac stimulating device as claimed in claim 1 wherein said pulse delivery controller varies said rate up to a maximum rate, and wherein said control circuit includes a timer connected to said first and second evoked response sensors for measuring at least one measured time gap selected from the group consisting of a first time gap between a stimulating pulse delivered to said first ventricle via said first electrode and the evoked response parameter thereto sensed by said first evoked response sensor, and a second time gap between a stimulating pulse delivered to said second ventricle via said second electrode and the evoked response parameter thereto sensed by said second evoked response sensor, and wherein said control circuit includes a monitor connected to said timer for monitoring said at least one measured time gap for a plurality of different rates produced as said pulse delivery controller varies said rate, and wherein said control circuit lowers said maximum rate if said at least one measured time gap does not decrease as said rate increases.

* * * * *